United States Patent
Kong et al.

(10) Patent No.: US 6,395,523 B1
(45) Date of Patent: May 28, 2002

(54) ENGINEERING NICKING ENDONUCLEASES FROM TYPE IIS RESTRICTION ENDONUCLEASES

(75) Inventors: Huimin Kong, Wenham; Caroline Besnier, Cambridge; Yan Xu, Beverly, all of MA (US)

(73) Assignee: New England Biolabs, Inc., Beverly, MA (US)

( * ) Notice: Subject to any disclaimer, the term of this patent is extended or adjusted under 35 U.S.C. 154(b) by 0 days.

(21) Appl. No.: 09/872,861

(22) Filed: Jun. 1, 2001

(51) Int. Cl.[7] .............................. C12N 9/00; C12P 21/04
(52) U.S. Cl. ........................................ 435/183; 435/69.1
(58) Field of Search ................................. 435/183, 199, 435/69.1

(56) References Cited

PUBLICATIONS

Stahl, F. et al., "Introduction of asymmetry in the naturally symmetric restriction endonuclease EcoRV to investigate intersubunit communication in the homodimeric protein", PNAS USA, vol. 93, pp. 6175–6180 (1996).*
Roberts and Macelis, Nucleic Acids Res. 26:338–350 (1998).
Heitman, Genetic Engineering, 15:57–107 (1993).
Kornberg and Baker, DNA Replication, 2nd edition, W.H. Freeman and Company, New York :(1992).
Geider, et al., J. Biol. Chem. 257:6488–6493 (1982).
Higashitani, et al., J. Mol. Biol. 237:388–400 (1994).
Modrich, J. Biol. Chem., 264:6597–6600 (1989).
Abdurashitov, et al., Mol. Biol. (Mosk) 30:1261–1267 (1996).
Walker, et al., Proc. Natl. Acad. Sci. USA 89:392–396 (1992).
Walker and Linn, Clin. Chem. 43:1604–1608 (1996).
Spears, et al., Anal. Biochm. 247:130–137 (1997).
Morrison & Desrosiers, Biotechniques 14:454–457 (1993).
Morgan, et al., Biol. Chem. 381:1123–1125 (2000).
Wah, et al., Nature 388:97–100 (1997).
Kim & Chandrasegaran, Proc. Natl. Acad. Sci. USA 91:883–887 (1994).
Kim, et al., Proc. Natl. Acad. Sci. USA 94:12875–12879 (1997).
Kim, et al., Biol. Chem., 379:489–495 (1998).
Wah, et al., Proc. Natl. Acad. Sci. USA 95:10564–10569 (1998).
Bitinaite, et al. Proc. Natl. Acad. Sci. USA 95:10570–10575 (1998).
Miller, A host course in bacterial genetics: A Laboratory Manual & Handbook for *E. coli* and related bacteria. Unit 4: Mutagenesis pp. 83–211, Cold Spring Harbor Laboratory Press, 1992.

* cited by examiner

*Primary Examiner*—Kenneth R. Horlick
*Assistant Examiner*—Teresa Strzelecka
(74) *Attorney, Agent, or Firm*—Gregory D. Williams

(57) ABSTRACT

The present invention relates to methods to engineer nicking endonucleases from existing Type IIs restriction endonucleases, and the production of the engineered nicking endonucleases. Two engineering methods are disclosed. One involves inactivating the dimerization function of a Type IIs restriction enzyme using site-directed mutagenesis approach. The other involves replacing the cleavage domain of a Type IIs restriction enzyme with the cleavage domain from a natural occurring nicking endonuclease, N.BstNBI.

7 Claims, 6 Drawing Sheets

FIG. 2

```
MlyI    MASLSKTKHLFGFTSPRTIEKIIPELDILSQQFSGKVW....G.ENQINF 45
        :|  . :   |||. ||| ||| :|. ||| |    |.| |
N.BstNBI ...MAKKVNWYVSCSPRSPEKIQPELKVLA.NFEGSYWKGVKGYKAQEAF 46

46 FDAIFNSDFYEGTTYPQDPALAARDRITRAP.KALGFIQL..KPVIQLTK 92
        :  |||| .: | . |||: || | ||: .  . :.:|.
 47 AKELAALPQFLGTTYKKEAAFSTRDRV...APMKTYGFVFVDEEGYLRITE 94

93 AGNQLVNQKRLPELFTKQLLKFQLPSPYH..TQSPTVNFNVRPYLELLRL 140
        || | | :| :.| |||.|.| || |  : |  ..: | ..| |
 95 AGKMLANNRRPKDVFLKQLVKWQYPSFQHKGKEYPEEEWSINPLVFVLSL 144

141 INELGSISKTEIALFFLQLVNYNKFDEIKNKILKFRETRKNNRSVSWKTY 190
        : ..| :|| :||:| |  | |. |||  .|:.|| |. :  . |
145 LKKVGGLSKLDIAMFCLTATNNNQVDEIAEEIMQFRNEREKIKGQNKKL. 193

191 VSQEFEKQISIIFADEVTAKNFRTRE.SSDESFKKFVKTKEGNMKDYADA 239
        || .         :.:    : || |||| |.:|| | :| |||
194 ...EFTENYFFKRFEKIYGNVGKIREGKSDSSHKSKIETKMRNARDVADA 240

240 FFRYIRGTQLVTIDKNLHLKISSLKQDSVDFLLKNTDRNALNLSLMEYEN 289
        || || |    | | :.  || | :|  :: ..    . |:
241 TTRYFRYTGLFVARGN.QLVLNPEKSDLIDEIISSSKVVKNYTRVEEFHE 289

290 YLFDPX..........QLI.....VLEXNSGL..........INSKIKQL 314
        |  .|        ||.    : |. |         .|. |
290 YYGNPSLPQFSFETKEQLLDLAHRIRDENTRLAEQLVEHFPNVKVEIQVL 339

315 DDSINVESLKID..DAKDLL...NDLEIQRKAKTIEDTVNHLKLRSDIED 359
        :| | . |:|   ||..:   :|::: || ::  |  :  ::  |
340 EDIYNSLNKKVDVETLKDVIYHAKELQLELKKKKLQADFNDPRQLEEVID 389

360 ILDVF........AKIKKRDVPDVPLFLEWNIWRAFAALNHTQAIEGNFI 401
        :|:|:       ||| | :.   || | | |. . ||:
390 LLEVYHEKKNVIEEKIKARFIANKNTVFEWLTWNGFIILGNALEYKNNFV 439

402 VDLDGMPLNTAPGKKPDIEINYGSFSCIVEVTMSSGETQFNMEGSSVPRH 451
        :| :  |.  | |.||.||| |  : ||| | ||| ||  |||
440 IDEELQPVTHAAGNQPDMEIIYEDFIVLGEVTTSKGATQFKMESEPVTRH 489

452 Y....GDLVRK.VDHDAYCIFIAPKVAPGTKAHFFNLNRLSTKHYGGKTK 496
        |    :| :. |: : ||:|||:.    |  | |.       |:
490 YLNKKKELEKQGVEKELYCLFIAPEINKNTFEEFMKYNIVQ......NTR 533

497 IIPMSLDDF..ICFLQVGITHNFQDINK...LKNWLDNLINFNLESEDEEI 542
        |||:||  |   .|  :    . :.  :|| :.|    :|  |  .
534 IIPLSLKQFNMLLMVQKKLIEKGRRLSSYDIKNLMVSLYRTTIECERKYT 583

543 WFEEIISK.ISTWAI....... 556
        . :  :. | :
584 QIKAGLEETLNNWVVDKEVRF  605
```

ENGINEERING NICKING ENDONUCLEASES FROM TYPE IIS RESTRICTION ENDONUCLEASES

BACKGROUND OF THE INVENTION

The present invention relates to methods for converting Type IIs restriction endonucleases into site specific nicking endonucleases. The engineering theme is based on a naturally existing nicking endonuclease, N.BstNBI, which is related to Type IIs restriction endonucleases. In general, Type IIs endonucleases bind to a specific sequence and cleave both DNA strands near, but not within the specific sequence. The double-stranded cleavage activity of N.BstNBI has been severely limited by natural mutations and thus it nicks only one strand of DNA under standard digestion conditions. In accordance with the present invention, new nicking endonucleases can be engineered from Type IIs endonucleases by either inactivating their second-strand cleavage activity or by swapping the cleavage domains between a target Type IIs enzyme and a known or engineered nicking enzyme.

Restriction endonucleases are enzymes that recognize and cleave specific DNA sequences. Usually there is a corresponding DNA methyltransferase that methylates and therefore protects the endogenous host DNA from digestion by its cognate restriction endonuclease. Restriction endonucleases can be classified into three groups based on cofactor requirements: Type I, II (including IIs), and III.

More than 3000 restriction endonucleases with over two hundred different specificities have been isolated from bacteria (Roberts and Macelis, *Nucleic Acids Res.* 26:338–350 (1998)). Type II and Type IIs restriction enzymes require only $Mg^{++}$ as cofactor; both cleave DNA at a specific position, and therefore are useful in genetic engineering and molecular cloning.

Most restriction endonucleases catalyze double-stranded cleavage of DNA substrate via hydrolysis of two phosphodiester bonds on opposite DNA strands (Heitman, *Genetic Engineering.* 15:57–107 (1993)). For example, Type II enzymes, such as EcoRI and EcoRV, recognize palindromic sequences and cleave both strands symmetrically within the recognition sequence. Type IIs endonucleases recognize asymmetric DNA sequences and cleave both DNA strands outside of the recognition sequence.

There are some proteins in the literature which break only one DNA strand and therefore introduce a nick into the DNA molecule. Most of those proteins are involved in DNA replication, DNA repair, and other DNA-related events (Kornberg and Baker, DNA replication. 2nd edit. W.H. Freeman and Company, New York, (1992)). For example, gpII protein of bacteriophage fI recognizes and binds a very complicated sequence at the replication origin of the phage genome. It introduces a nick in the plus strand to initiate rolling circle replication; it is also involved in ligating the displaced plus strand to generate single-stranded circular phage DNA. (Geider et al., *J. Biol. Chem.* 257:6488–6493 (1982); Higashitani et al., *J. Mol. Biol.* 237:388–400 (1994)). Another example is the MutH protein, which is involved in DNA mismatch repair in *E. coli*. MutH binds at dam methylation site (GATC), where it forms a protein complex with nearby MutS which binds to a mismatch.

The MutL protein facilitates this interaction, triggering single-stranded cleavage by MutH at the 5' end of the unmethylated GATC site. The nick is then translated by an exonuclease to remove the mismatched nucleotide (Modrich, *J. Biol. Chem.* 264:6597–6600 (1989)).

The nicking enzymes mentioned above are not very useful in the laboratory for manipulating DNA due to the fact that they usually recognize long, complicated sequences and/or are associated with other proteins to form protein complexes which are difficult to manufacture and use. None of these nicking proteins are commercially available. The nicking enzyme N.BstNBI, was found from the thermophilic bacterium *Bacillus stearothermophilus* (Morgan et al., *Biol. Chem.* 381:1123–1125 (2000); U.S. Pat. No. 6,191,267). N.BstNBI is an isoschizomer of N.BstSEI (Abdurashitov et al., *Mol. Biol.* (Mosk) 30:1261–1267 (1996)). Unlike gpII and MutH, N.BstNBI behaves like a restriction endonuclease. It recognizes a simple asymmetric sequence, 5'-GAGTC-3', and it cleaves only one DNA strand, 4 bases away from the 3'-end of its recognition site, without interaction with other proteins.

Because N.BstNBI acts more like a restriction endonuclease, it should be useful in DNA engineering. For example, it can be used to generate a DNA substrate containing a nick at a specific position. N.BstNBI can also be used to generate DNA with gaps, long overhangs, or other structures. DNA templates containing a nick or gap are useful substrates for researchers in studying DNA replication, DNA repair and other DNA related subjects (Kornberg and Baker, DNA replication. 2nd edit. W.H. Freeman and Company, New York, (1992)). One potential application of the nicking endonuclease is its use in strand displacement amplification (SDA), which is an isothermal DNA amplification technology. SDA provides an alternative to polymerase chain reaction (PCR). It can reach $10^6$-fold amplification in 30 minutes without thermo-cycling. SDA uses a restriction enzyme to nick the DNA and a DNA polymerase to extend the 3'-OH end of the nick and displace the downstream DNA strand (Walker et al., *Proc. Natl. Acad. Sci. USA.* 89:392–396 (1992)). The SDA assay provides a simple (no temperature cycling, only incubation at 60° C.) and very rapid (as short as 15 minutes) detection method and can be used to detect viral or bacterial DNA. SDA is being introduced as a diagnostic method to detect infectious agents, such as Mycobacterium tuberculosis and Chlamydia trachomatis (Walker and Linn, *Clin. Chem.* 42:1604–1608 (1996); Spears, et al., *Anal. Biochem.* 247:130–137 (1997)).

For SDA to work, a nick has to be introduced into the DNA template by a restriction enzyme. Most restriction endonucleases make double-stranded cleavages. Therefore, in previous work, substituted α-thio deoxynucleotides (dNTPαS) have been incorporated into the DNA. Many restriction endonucleases will not cleave phosphodiester bonds with (α-thio substitutions. Thus the endonuclease only cleaves the un-substituted linkages which are designed to be within the primer region. The (α-thio deoxynucleotides are eight times more expensive than regular dNTPs (Pharmacia), and are not incorporated well by the Bst DNA polymerase as compared to regular deoxynucleotides (J. Aliotta, L. Higgins, and H. Kong, unpublished observation). Alternatively, if a nicking endonuclease were to be used in SDA, it would introduce a nick into the DNA template naturally. Thus the dNTPαS would no longer be needed for the SDA reaction when a nicking endonuclease is being used. This idea has been tested, and the result agreed with our speculation. The target DNA can be amplified in the presence of the nicking endonuclease N.BstNBI, dNTPs, and Bst DNA polymerase (U.S. Pat. No. 6,191,267).

There is an increasing demand for more nicking endonucleases, because they are useful in SDA and other DNA engineering applications. We have cloned and characterized the nicking endonuclease N.BstNBI and our results show that N.BstNBI is a naturally mutated Type IIs endonuclease with diminished double-stranded cleavage activity (U.S. Pat. No. 6,191,267). The natural occurrence of this type of endonuclease may be quite limited; in any event, assay methods to detect them unambiguously are not available. So far only two nicking endonucleases have been reported and both recognize same specificity (U.S. Pat. No. 6,191,267). The methods disclosed herein provide a novel approach for generating new nicking endonucleases using a protein engineering approach.

Effort has been long taken to engineer novel endonucleases with little success. FokI is a Type IIs restriction enzyme which exhibits a bipartite nature, an N-terminal DNA recognition domain and a C-terminal DNA cleavage domain (Wah et al., Nature 388:97–100 (1997)). The modular nature of FokI led to the invention of several enzymes with new specificities by substituting other DNA binding proteins for the recognition domain. Fusion of the Ubx homeodomain to the FokI cleavage domain yielded an enzyme that cleaves on both sides of the Ubx recognition site (Kim and Chandrasegaran, *Proc. Natl. Acad. Sci. U.S.A.* 91:883–887 (1994)). Similar approaches have been utilized to create enzymes that can cleave near Z-DNA (Kim et al, *Proc. Natl. Acad. Sci. U.S.A.* 94:12875–12879 (1997)), and the Gal4 recognition site (Kim et al., *Biol. Chem.* 379:489495 (1998)). However, two major drawbacks are associated with such chimeric enzymes. First, the chimeric enzymes cleave at multiple sites on both sides of the recognition sequence; therefore, the cleavage specificity is much relaxed. Second, the enzymatic cleavage activity of the chimeric enzymes is very low.

The dimerization interface of FokI is formed by the parallel helices, α4 and α5, located less than 10 amino acid residues away from its catalytic site of PD—DTK (Wah et al., *Proc. Natl. Acad. Sci. USA.* 95, 10564–10569 (1998)). Changing D483A and R487A in the α4 helix greatly impaired the DNA cleavage activity of FokI (Bitinaite et al., *Proc. Natl. Acad. Sci. USA.* 95, 10570–10575 (1998)).

In this patent, protein engineering approaches and methods that lead to creation of highly sequence-specific and highly active nicking endonucleases are disclosed. In the first example, a method for engineering a nicking enzyme by disrupting the dimerization domain of the Type IIs endonuclease MlyI is disclosed. In the second example, a method for converting the Type IIs endonucleases AlwI into a nicking enzyme using domain swapping approach is disclosed.

SUMMARY OF THE INVENTION

In accordance with the present invention, methods are provided for converting Type IIs restriction endonucleases into nicking endonucleases. In its simplest form, the method comprises identifying a suitable double-stranded nuclease followed by mutation of the dimerization interface responsible for double-stranded cleavage such that the mutated nuclease cleaves only one DNA strand at a specific location within or adjacent the recognition sequence.

In one preferred embodiment, the mutation occurs by substituting one or more amino acid residues required for dimerization/cleavage. In one particularly preferred embodiment illustrating the approach, the Type IIs restriction endonuclease MlyI is mutated by amino acid alteration.

Type IIs restriction endonuclease MlyI recognizes the same GAGTC sequence as N.BstNBI does, but MlyI cleaves both DNA strands 5 bases from the recognition site, while N.BstNBI only cleaves the top strand, 4 bases from the recognition site (FIG. 1A & B). Two amino acid residues (Tyr491 and Lys494) were changed to alanines, which resulted in a nicking endonuclease, N.MlyI. The engineered N.MlyI still recognizes the same GAGTC sequence, but it cleaves only the top strand, 5 bases downstream from GAGTC (FIG. 1C).

In another preferred embodiment, the mutation comprises swapping or substituting the region containing the dimerization interface with one known to be dimerization-defective resulting in cleavage of one, not both, DNA strands. In a particularly preferred embodiment, the dimerization interface of AlwI is replaced by the corresponding domain from N.BstNBI. The Type IIs endonuclease AlwI recognizes GGATC sequence, which is different than the GAGTC sequence recognized by N.BstNBI (FIG. 1D). The dimerization domain of AlwI was replaced by the corresponding domain in N.BstNBI (FIG. 3). The resulting chimeric endonuclease recognizes the same GGATC sequence that AlwI recognizes, but the engineered N.AlwI cleaves on one DNA strand just like the nicking enzyme N.BstNBI (FIG. 1E). Both engineered N.MlyI and N.AlwI are very active, sequence-specific, and strand-specific nicking enzymes.

BRIEF DESCRIPTION OF THE DRAWINGS

FIG. 2 shows the amino acid sequence alignment between Type IIs restriction endonuclease MlyI (top sequence; GenBank Accession No. AF355462, SEQ ID NO:3) and the nicking endonuclease N.BstNBI (bottom sequence; GenBank Accession No. AF329098, SEQ ID NO:4).

FIG. 5 shows the characterization of DNA cleavage activity of the chimeric nicking endonuclease N.AlwI.

DETAILED DESCRIPTION OF THE INVENTION

Figure 1:
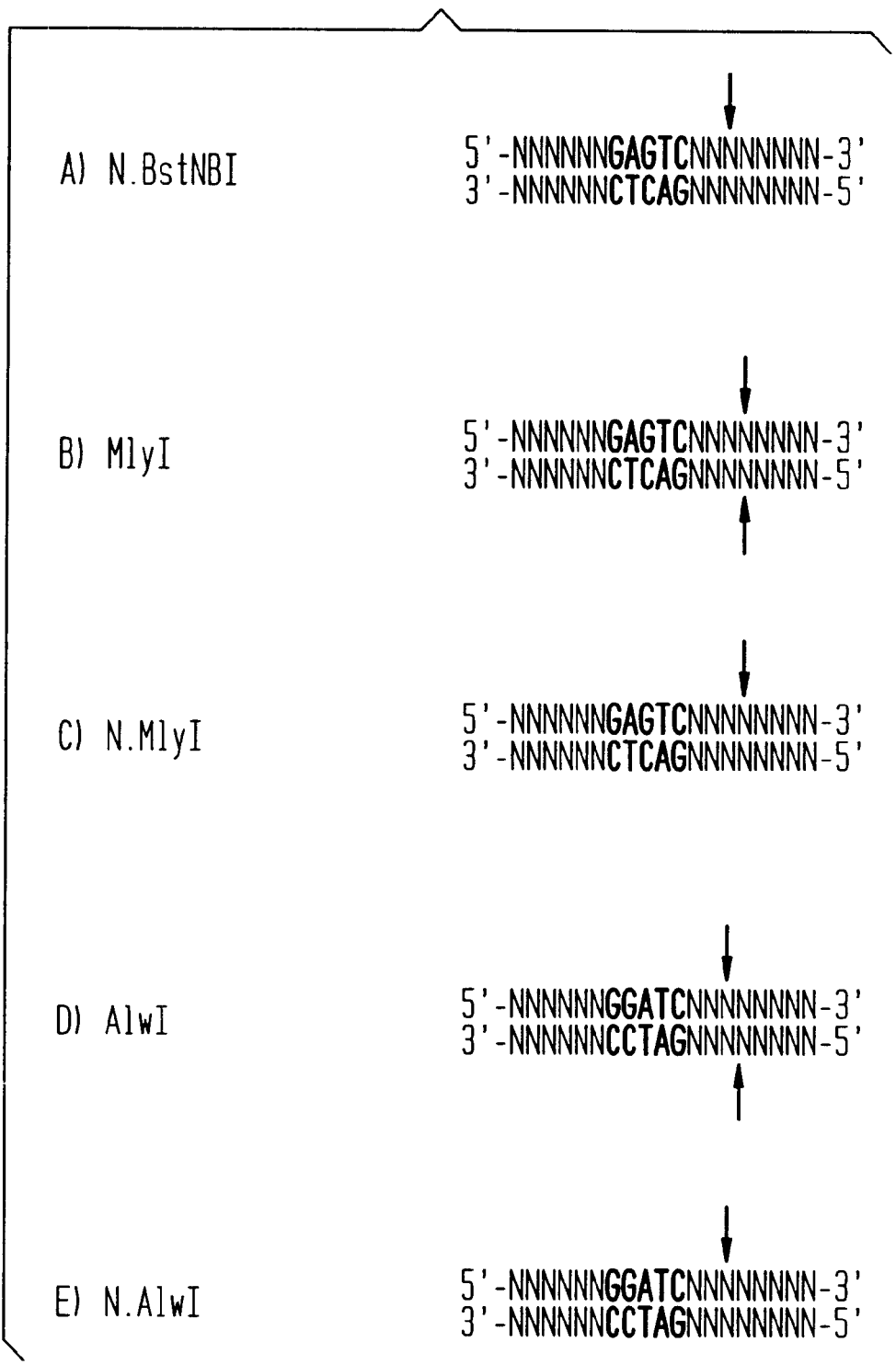
FIG. 1 shows the recognition sequences and sites of cleavage of N.BstNBI nicking endonuclease (FIG. 1A, SEQ ID NO:1), Type IIs restriction endonuclease MlyI (FIG. 1B, SEQ ID NO:1), the engineered nicking endonuclease N.MlyI (FIG. 1C, SEQ ID NO:1), Type IIs restriction endonuclease AlwI (FIG. 1D, SEQ ID NO:2), and the chimeric nicking endonuclease N.AlwI (FIG. 1E, SEQ ID NO:2). Recognition sequences are shown in bold type and cleavage sites are indicated by arrows.

The present invention relates to a method for creating nicking endonucleases, which cleave DNA on one strand only at a specific location in or near a specific recognition sequence. In its simplest form, this method comprises identifying a suitable double-stranded nuclease, followed by mutating the dimerization interface that is needed for double-strand cleavage such that only cleavage of one strand occurs. The mutation may comprise either alteration of one or more residues required for dimerization or substitution of the region containing the dimerization interface with a corresponding region known to be dimerization-defective. In another preferred embodiment, both types of mutations may be employed to achieve the desired result.

In one embodiment of this method, an existing restriction endonuclease of Type IIs, cleaving both DNA strands at particular locations relative to a recognition site, is modified to cleave one strand only.

The invention preferably begins with a Type IIs endonuclease similar to the examples studied, such as MlyI and AlwI, in which an N-terminal sequence-specific DNA binding moiety is joined with a C-terminal sequence-non-specific cleavage moiety by one or more amino acids.

More preferably, the starting endonuclease is one which cleaves in two sequential steps, such that a small amount of nicked intermediate is observed during the course of double-strand cleavage.

The method of the present invention provides various means to identify locations in the cleavage moiety that will enable inactivation of the second-strand cleavage activity.

In a preferred embodiment of this aspect of this invention, an advantageous procedure is to create a multiple alignment of the amino acid sequence of the cleavage moiety of the target enzyme with those of related enzymes, particularly N.BstNBI, to enable identification of candidate residues critical to dimerization function that is required for second-stand cleavage, followed by assessment of suppression of the second-strand cleavage activity.

In another embodiment of this aspect of this invention where multiple alignments fail to identify a critical dimerization region, an alternative procedure is to create mutations randomly through the cleavage moiety of the target enzyme, followed by assessment of suppression of the second-strand cleavage activity.

The method of the present invention also provides a dimerization-defective cleavage moiety that may be substituted for the cleavage moiety of a dimerization-competent endonuclease to enable selective inactivation of second-strand cleavage activity. In one preferred embodiment, an advantageous procedure is to create a multiple alignment of the amino acid sequence of the cleavage moiety of the target enzyme with those of related enzymes to enable identification of the border of the sequence-recognition moiety and the cleavage moiety. In a particularly preferred embodiment, only that portion of the cleavage domain containing the dimerization surface is subject to substitution.

In another embodiment, the present invention also provides a nicking enzyme derived from the restriction enzyme MlyI, with recognition site GAGTC, and cleavage after the fifth base 3' to the recognition site.

In yet another embodiment, the present invention also provides a nicking enzyme derived from AlwI, with recognition sequence GGATC, and cleavage after the fifth base 3' to the recognition site.

In general, the following steps can be used to convert a Type IIs endonuclease into a nicking enzyme by one or more amino acid substitutions:

Step 1. Clone and sequence the gene which encodes the target Type IIs endonuclease and perform sequence alignment.

Step 2. If the target Type IIs endonuclease does share sequence similarity with characterized Type IIs restriction endonucleases, preferably with the nicking enzyme N.BstNBI, the cleavage moiety and dimerization moiety of the target endonuclease can be revealed by the sequence alignment. If not, see below.

Step 3. Once the potential cleavage/dimerization moiety is located, the conserved charged amino-acid residues with the moiety are preferably substituted by a neutral amino acid such as alanine. The phenotypes of these mutants are then screened for the ability to cleave only one DNA strand (See the example of MlyI below).

Alternatively the domain swapping method can be used alone or in parallel with amino acid substitution method. The domain swapping approach comprises the following steps:

Step 1. Clone and sequence the gene which encodes the target Type IIs endonuclease and perform sequence alignment.

Step 2. If the target Type IIs endonuclease does share sequence similarity with characterized Type IIs restriction endonucleases, preferably with the nicking enzyme N.BstNBI, the cleavage moiety and dimerization moiety of the target endonuclease can be revealed by the sequence alignment. If not, see below.

Step 3. Once the potential cleavage/dimerization moiety is located, it can be replaced with a corresponding moiety from a nicking endonuclease such as N.BstNBI. Both naturally-occurring as well as engineered nicking endonucleases may be used for this purpose. The phenotypes of these swapping mutants can be screened for the ability to cleave only one DNA strand (See the example of AlwI below).

The amino acid substitution and domain swapping method can be used separately or in conjunction with each other.

If the target Type IIs endonuclease does not share any sequence similarity with characterized Type IIs endonucleases, random mutagenesis can be used. In general, one or more of the following approaches can be used to perform mutagenesis of the target Type IIs endonuclease.

In the absence of information from an alignment procedure, the following steps may be used to reveal nicking enzymes. The procedure depends on three assumptions. First, if a mutation abolishes the dimerization function, the mutated endonuclease may only exist as a monomer and thus cleaves only one DNA strand. Such a mutant should be viable in the presence of lower levels of protective methylation than would be the wild type gene, even perhaps in its absence. Second, an enzyme with a nicking activity would nevertheless inflict damage on the host cell's DNA that would be detected by the DNA-damage-response (SOS) system, and third, that high levels of DNA ligase would enable the host cell to evade the SOS-response in the presence of such a nicking endonuclease.

In a preferred embodiment, a first, random mutagenesis can be used to generate candidates lacking double-stranded cleavage activity. For example, DNA the enzyme can be treated with hydroxylamine, which introduces C/T transitions into DNA template, or can be grown in cells that have high rates of forward mutagenesis, such as mutS or mutD strains of *E. coli*; or cells can be grown in the presence of an alkylating agent, such as ethyl methane sulfonate, or can be treated with ultraviolet light (Miller, Jeffrey H. A short course in bacterial genetics: A laboratory manual and handbook for *Escherichia coli* and related bacteria. Unit 4: mutagenesis. pp.83–211, Cold Spring Harbor Laboratory Press, 1992.). Mutations that greatly reduce or abolish DNA cleavage can be isolated by transforming the mutagenized pool into a host strain lacking the protective modification methyltransferase, or more preferably, expressing it at a level that protects the DNA incompletely.

Thereafter, a genetic screening method, the "endo-blue" method, can be used to screen among the survivors for mutants expressing DNA nicking activity. Following random mutagenesis and selection for the loss of function mutants, three types of the loss of function mutants may be generated: 1) completely inactive; 2) loss of DNA cleavage but still able to bind to DNA; 3) loss of double stranded DNA cleavage activity but still able to cleave one DNA strand (nicking activity). Limited expression of a endonuclease gene in *E. coli* cells (ER1992 with dinD1::LacZ+ fusion) without the corresponding methylase can damage the DNA in vivo and induces the SOS response, resulting in the SOS-induced blue colonies on indicator plates containing X-gal (U.S. Pat. No. : 5, 498,535). The 'Endo-blue' selection method has been successfully used to directly clone several thermophilic restriction endonuclease genes at New England Biolabs (Beverly, Mass., USA). In this instance, the pool of genes that survive in the absence of the protective methyltransferase, or in the presence of low levels of the methyltransferase, would be transformed into this strain or a similar on, with or without low levels of methyltransferase, and those clones still able to induce blue color would be retained for further study.

Finally, to identify clones expressing DNA nicking activity, DNA plasmids recovered from the loss of function selection step and still able to induce the SOS response (and therefore neither null mutants nor mutants defective in DNA binding) are screened for the ability to nick DNA using a plasmid substrate containing a single site for the double-stranded endonuclease, as described in the foregoing descriptions of N.AlwI and N.MlyI.

The present invention is more fully described hereinbelow by application of the methods to two target Type IIs endonucleases, MlyI and AlwI. The dimerization function of Type IIs restriction endonuclease MlyI was inactivated by substitution of key amino acid residues in the cleavage-dimerization domain. The Type IIs endonuclease AlwI cleavage-dimerization domain was replaced by the corresponding domain from N.BstNBI, in which the dimerization surface is inactive.

1. Converting the Type IIs endonuclease MlyI into a nicking endonuclease by site-directed mutagenesis in its dimerization domain.

The Type IIs restriction endonuclease MlyI recognizes the same GAGTC sequence as N.BstNBI does, but MlyI cleaves both DNA strands while N.BstNBI only cleaves the top strand (FIG. 1A & B). MlyI shares significant sequence similarity with N.BstNBI (45.3% sequence similarity and 32.1% sequence identity, FIG. 2). The time course of cleavage reactions showed that MlyI cleave two strands of DNA in a sequential fashion with the DNA first being nicked and then further digested to the final linear form. In the case of the nicking endonuclease N.BstNBI, its second- strand cleavage activity was impaired probably, by natural mutations, and thus the nicked DNA was not efficiently converted into the linear DNA. This resulted in the accumulation of nicked DNA under normal digestion conditions. Gel filtration experiments showed that MlyI formed dimers in the presence of DNA and $Mg^{++}$ and in the same condition no dimers of N.BstNBI was observed (C. Besnier and H. Kong, unpublished results). This suggests that the second strand cleavage activity is probably mediated through dimerization as is the case for FokI. Based on this model, it was postulated that such Type IIs endonucleases could be converted into nicking endonuclease by disrupting their dimerization functions via mutagenesis.

The inferred dimerization helices of MlyI corresponding to helices of $\alpha 4$ and $\alpha 5$ of FokI were identified by sequence alignment between the cleavage domains of these endonucleases and the model enzyme FokI (not shown). In a first approach, nine potential-dimerization residues were individually changed to alanines in MlyI, within or near the putative $\alpha 4$ helix (indicated by underline in FIG. 2). The mutants were still able to perform double stranded DNA cleavage. Thus, this alignment procedure was not sufficient to identify the critical residues. The $\alpha 5$ helix was then examined. Multiple sequence alignment at the putative $\alpha 0:5$-helix region revealed a YGGK motif, which exists in MlyI and PleI (not shown) but not in N.BstNBI (FIG. 2, highlighted in bold type). Tyr and Lys residues were changed to Ala in the YGGK motif of MlyI.

A mutant construct expressing MlyI-Y491A/K494A (designated N.MlyI, see below) in plasmid pUC19 was made using a PCR-mediated mutagenesis method (Morrison and Desrosiers, *Biotechniques* 14:454–457 (1993)). The recombinant plasmid was sequenced to confirm the desired double mutations and to check for PCR errors. Preliminary activity tests with crude cell extracts containing the mutated MlyI were promising. The N.MlyI protein was purified for more accurate tests. Purification steps included an anion exchanger, a cation exchanger and two affinity columns. The purity of the final sample was tested on a SDS-polyacrylamide gel. N.MlyI represented more than 95% of the total protein.

Figure 4A:
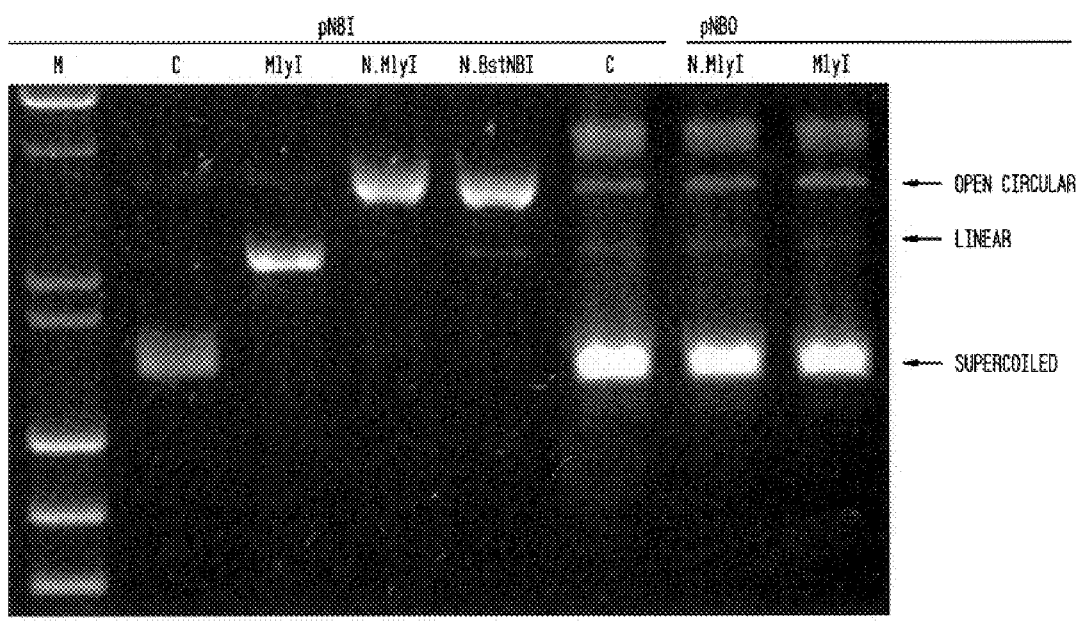
FIG. 4 shows the characterization of DNA cleavage activity of the engineered N.MlyI nicking endonuclease. A) Agarose gel electrophoresis showing plasmid pNB 1 undigested (C=control), digested by MlyI, N.MlyI and N.BstNBI. Plasmid pNBO was also used as a specificity control either undigested (C), digested by N.MlyI or MlyI. M=Molecular weight marker (Lambda DNA/ HindIII and φX174/HaeIII). B) Determination of the cleavage sites of N.MlyI. Plasmid pUC19 that contains a GAGTC recognition sequence and two synthetic primers were used in sequencing reactions based upon the dideoxy-nucleotide chain termination method. Additional extension reactions were carried out with the same plasmid and primer in the presence of four deoxynucleotides and [$^{33}$P] dATP. The labeled substrate was then digested with MlyI or the engineered N.MlyI. After the digestion, the reaction mixture was divided into two aliquots: one was mixed with stop solution immediately (lane Klenow–); the other was treated with Klenow fragment at room temperature for 10 minutes and then mixed with stop solution (lane Klenow+). The cleavage reaction products were then separated on an 8% denatured polyacrylamide gel along with standard A, C, G, T ladders, and detected by autoradiography.

The purified N.MlyI was tested with lambda DNA. No double stranded DNA cleavage was detected. The nicking activity of N.MlyI was further examined using plasmid DNAs. The supercoiled form of an undigested plasmid can be converted into a nicked closed circular form when one strand is cleaved by a nicking endonuclease, or into a linear form when both strands are cleaved in proximity by a restriction enzyme. When plasmid pNB1 (containing one MlyI recognition site) was used in the digestion assay, pNB1 was converted into a nicked open circular form by N.MlyI and the nicking enzyme N.BstNBI, and into linear form by the wild type MlyI (FIG. 4A). When plasmid pNB0 (containing no MlyI site) was used in the same assay, pNB0 remained in the supercoiled form following the digestions (FIG. 4A). This result suggested that the nicking activity of N.MlyI was sequence specific. N.MlyI activity was titrated using pNB1. One unit was defined as the amount of N.MlyI needed to achieve complete nicking of one µg of pNB1 in one hour at 37° C. The specific activity of the mutated MlyI was approximately 400,000 units per mg of protein, which is very similar to that of the wild-type MlyI (when a unit is defined as the amount of MlyI needed to achieve complete digestion of one µg of pNB1 in one hour at 37° C.).

Figure 4B:
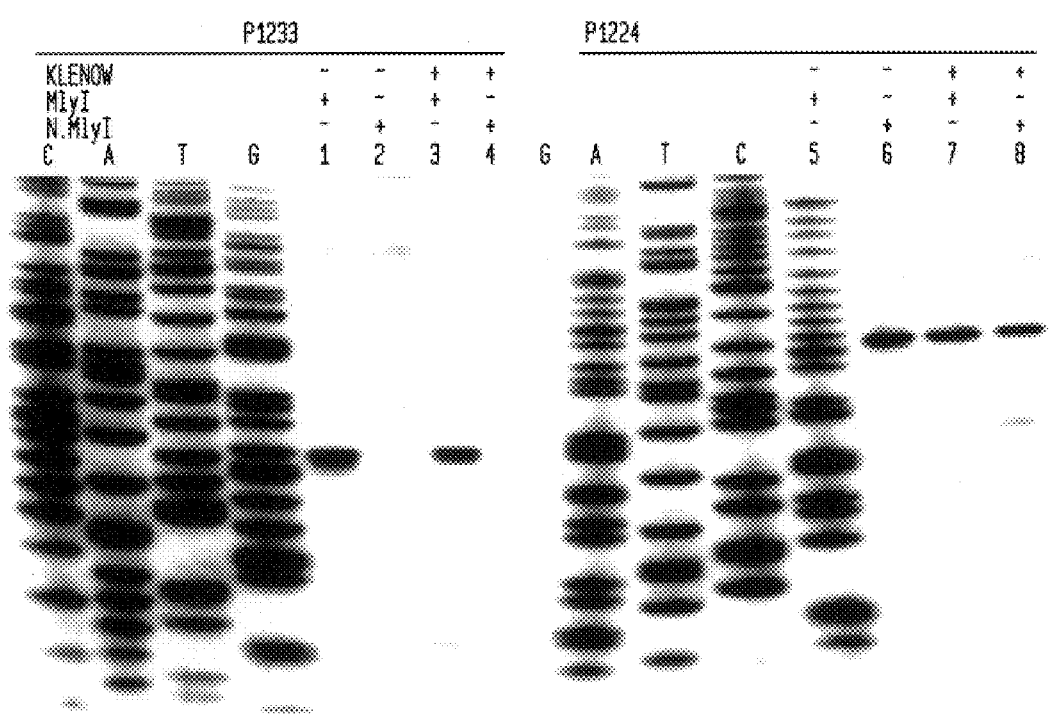

To determine the cleavage position of N.MlyI precisely, the cleavage site on each DNA strand was mapped by comparing dideoxy sequencing ladders with polymerized extension products digested with engineered N.MlyI as well as the wild-type MlyI. Plasmid pUC19 was used as template and two primers were employed, primer 1224 for the top strand and primer 1233 for the bottom strand (FIG. 4B). The extension products of the top strand were cleaved five base pairs on the 3' side of the 5'-GAGTC-3' sequence by both MlyI (FIG. 4B, lane 5) and N.MlyI (FIG. 4B, lane 6). The bottom strand was cleaved by only MlyI (FIG. 4B, lane 1), but not by the N.MlyI endonuclease (FIG. 4B, lane 2). The results from the sequencing gel show that N.MlyI cleaves the top strand only, and that the cleavage site is located 5 base pairs to the 3' side of its recognition sequence. When the Klenow fragment of *E. coli* DNA polymerase I was added to the digested products, no further extension was detected for the MlyI-cleaved fragment, demonstrating that MlyI cleavage generates blunt-ended fragments (FIG. 4B, lanes 3 & 7). However in the case of N.MlyI, the cleavage band was extended to a much large-size band (beyond the display window in FIG. 4B) by the Klenow fragment in a nick translation reaction (FIG. 4B, lane 8), which further supports the existence of a nick on the N.MlyI cleaved DNA. These results showed that the engineered N.MlyI is an active, sequence-specific, and strand-specific nicking endonuclease.

2. Converting the Type IIs endonuclease AlwI into a nicking endonuclease by swapping the dimerization domain of AlwI with the non-functional dimerization domain from N.BstNBI.

The deduced polypeptide sequences of AlwI and N.BstNBI show 28.7% sequence identity and 41.5% similarity. Previous results suggest that the double-stranded cleavage activity of a Type IIs endonuclease is dependent on dimerization. To convert AlwI into a nicking endonuclease, the dimerization domain of AlwI was swapped with the non-functional domain of N.BstNBI. It was hypothesized that this would lead to a chimeric endonuclease which recognize the AlwI recognition sequence but with the cleavage characteristics of the nicking enzyme N.BstNBI. This was successfully demonstrated by one of the two attempts described below.

Figure 3:
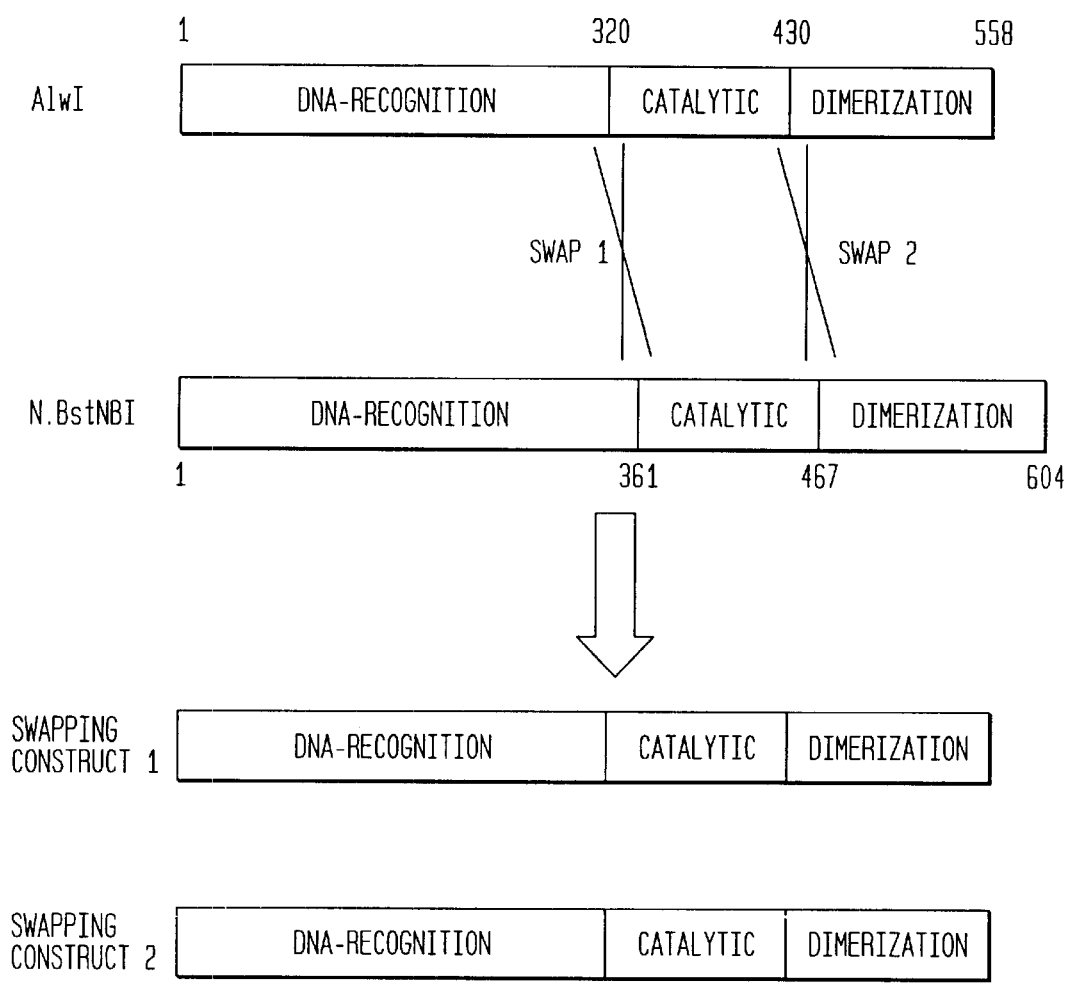
FIG. 3 shows a schematic diagram of domain-swapping method to produce the chimeric nicking endonuclease N.AlwI. The numbers indicate positions of amino acid residues. Crosses indicate swapping points.

To maximize the chance of success, two swapping points were chosen. One swap construct was made by fusing the putative DNA recognition domain of AlwI (located on the N-terminal half, residues 1 to 320) to the C-terminal region of N.BstNBI (including both the putative catalytic and dimerization domains, residues 361 to 604; FIG. 3). However, this chimeric protein (FIG. 3, Swapping Construct 1) exhibited no detectable cleavage activity (data not shown). Swapping at this junction might have disrupted protein folding and resulted in a completely inactive enzyme. In a different context, therefore this approach may work.

The other chimeric enzyme, as shown in FIG. 3 Swapping Construct 2, was constructed by fusing a longer N-terminal part of AlwI (residues 1 to 430), including both its putative DNA binding domain and catalytic center, to the putative dimerization domain of N.BstNBI at the extreme C-terminal end (residues 467 to 604). This chimeric endonuclease, containing the dimerization domain from N.BstNBI, showed DNA nicking activity and was named N.AlwI. N.AlwI was expressed and purified to about 80% homogeneity.

The nicking activity of N.AlwI was first examined by using plasmid DNAs. To test whether the nicking activity of N.AlwI is sequence-dependent, two plasmids were constructed: pAC1 with one and pAC0 with no AlwI recognition sequence. Plasmids pAC0 and pAC1 contain two and three N.BstNBI recognition sites, respectively. As expected, the supercoiled pAC0 (FIG. 5A, lane 1) was not digested by AlwI (lane 2) or by N.AlwI (lane 3), but was nicked by N.BstNBI (lane 4). When plasmid pAC1 (lane 5) was incubated with the wild type AlwI, the supercoiled form was converted into the linear form (lane 6). In contrast, when pAC1 was incubated with the engineered N.AlwI, the supercoiled form was converted into a nicked open-circular form (lane 7), which migrated at the same position as the relaxed form produced by N.BstNBI (lane 8). These results demonstrate that the nicking activity of N.AlwI is dependent on the presence of the 5'-GGATC-3' sequence.

To precisely map the cleavage site of N.AlwI, the N.AlwI cleavage products were compared to sequencing ladders in a modified sequence reaction. As illustrated in FIG. 5B, both AlwI and N.AlwI cut the top strand; the cleavage site was located four bases downstream of the recognition site 5'-GGATC-3' in both cases. The wild type AlwI cut the bottom strand as well, but N.AlwI did not (FIG. 5C). Thus, the nicking site of N.AlwI is located on the top strand, four bases away from the recognition sequence (5'-GGATCNNNN-3').

The present invention is further illustrated by the following Examples. These Examples are provided to aid in the understanding of the invention and are not construed as a limitation thereof.

The references cited above and below are incorporated by reference herein.

EXAMPLE 1

Converting the Type IIs Endonuclease MlyI into a Nicking Enzyme by PCR Mediated Mutagenesis and Purification of the Engineered MlyI.

1. PCR site-directed mutagenesis of the MlyI endonuclease gene:

Based on the sequence comparison between the last 180 amino acids of PleI, MlyI, N.BstNBI and FokI, a tyrosine and a lysine were identified as residues potentially involved in the dimerization process. They belong to a short region (5 amino acids), which seems to be deleted in N.BstNBI, but conserved in PleI, MlyI and FokI. The tyrosine and the lysine were both changed to alanine in order to have a dramatic decrease of the dimerization function if those two residues turned out to be key residues for the dimerization.

The PCR site directed mutagenesis was performed according to the procedure of Morrison and Desrosiers (Morrison, H. and Desrosiers, R., Biotechniques 14:454–7 (1993)).

The first round of PCR was composed of two separate reactions carried out on pUC19-MlyIR clone (GeneBank Accession No. AF355462).

One reaction to amplify the section between the 5' end of the endonuclease gene and the mutation site was conducted, using the following primers:

```
5'-TTAAGCTTAAGGAGGTGATCTAATGGCATCGTTATCAAAGACT-3' (SEQ ID NO:5)
        (228-22)

5'-GGAATAATCTTTGTTGCTCCACCAGCATGT-3'             (SEQ ID NO:6)
        (7508-022)
```

The oligonucleotide primer 228-22 contains an HindIII site to facilitate cloning, a conserved ribosome binding site (RBS), an ATG start codon and 18 nucleotides complementary to the MlyIR 5'-end for hybridization. The oligonucleotide primer 7508-022 is the reverse mutagenic primer, which will introduce both Y491A and K494A mutations.

The other reaction, to amplify the section between the mutation site and the 3'-end of the endonuclease gene, was carried out using the following primers:

```
                                                    (SEQ ID
                                                     NO:7)
5'-ATITCTAGACTATATAGCCCATGTAGAAATTT-3'
        (228-23)

(SEQ ID
                                                     NO:8)
5'-ACATGCTGGTGGAGCAACAAAGATTATTCC-3'
        (7508-021)
```

The oligonucleotide primer 228-23 contains a XbaI site to facilitate cloning, a stop codon and 23 nucleotides complementary to the MlyIR 3'-end for hybridization. 7508-021 is the forward mutagenic primer, which will introduce both Y491A and K494A mutations.

The PCR reaction was carried out by combining:

10 µl 10X Taq Polymerase Buffer
10 µl of 2mM dNTPs
1 (100 ng) pUC19-MlyIR clone
1 µl (150 ng) primer 228-22 (reaction 1) or 228-23 (reaction 2)
1 µl (150 ng) primer 7508-022 (reaction 1) or 7508-021 (reaction 2)
74 µl dH$_2$O
1 µl (0.05 units) Deep Vent® polymerase
1 µl (5 units) Taq DNA polymerase and amplifying for 15 cycles at 95° C. for 30 seconds, 50° C. for 1 minute and 72° C. for 2 minutes. The resulting DNA fragments were purified using the QIAquick PCR Purification Kit (Qiagen).

The second round of PCR used as templates the first round DNA fragments from reaction 1 and reaction 2, with an 1:1 molar ratio, plus the primers corresponding to the 5'- and the 3'- end of MlyIR:

10 µl 10X Taq Polymerase Buffer
10 µl of 2mM dNTPs
1 µl (88 ng) of the MlyIR fragment from reaction 1
1 µl (12 ng) of the MlyIR fragment from reaction 2
1.5 µl (150 ng) primer 228-22
1.5 µl (150 ng) primer 228-23
73 µl dH$_2$O
1 µl (0.05 units) Deep Vent® polymerase
1 µl (5 units) Taq DNA polymerase and amplifying for 15 cycles at 95° C. for 30 seconds, 50° C. for 1 minute and 72° C. for 2 minutes. The resulting DNA fragments were purified using the QIAquick PCR Purification Kit (Qiagen). Those two PCR rounds provided full-length endonuclease gene with the two expected mutations (Y491A and K494A).

The second-round amplification product (MlyIR PCR product) and 1 µg of pUC19 were both digested with 20 units of HindIII and 20 units of XbaI, supplemented with 0.1 mg/ml BSA in 1X NEB Buffer 2 in a 50 µl reaction that was incubated at 37° C. for one hour. The digests were run on a 1% Low-Melting Point Agarose Gel (Genomic Performance Grade, American Bioanalytical). The PCR and vector DNA bands were excised and the gel slices were incubated at 65° C. for 10 min. The temperature was reduced to 40° C. and an in-gel ligation was performed by combining the following at 40° C.:

25 µl MlyIR PCR product (250 ng)
5 µl prepared pUC19 (100 ng)
5 µl 10X T4 DNA Ligase Buffer
2 µl β-Agarase (2 units)
1 µl T4 DNA Ligase (400 units)
12 µl dH$_2$O The reaction was incubated at 37° C. for one hour, then followed by an overnight incubation at 16° C. Five µl of the ligation reaction were transformed into E. coli strain ER2502 previously modified with the N.BstNBI methylase gene (approximately 107 cells). Individual colonies were isolated and analyzed by digesting minipreps (Qiagen QIAprep spin Miniprep kit) with the cloning enzymes to ensure that the MlyIR had indeed been cloned into the vector:

3 µl miniprep
2 µl 10X NEB Buffer 2
2 µl BSA (1 mg/ml)
1 µl HindIII (20 units)
1 µl XbaI (20 units)
11 µl dH$_2$O The digests were incubated at 37° C. for one hour.

2. Purification of N.MlyI (Y491A/K494A MlyI).

E. coli ER2502 previously modified with the N.BstNBI methylase gene and containing pUC19-MlyIR-Y491A/K494A was grown at 37° C. in 24 liters of LB medium supplemented with 0.1 mg/ml ampicillin. The cells were harvested by centrifugation. All the following procedures were performed on ice or at 4° C. 109 g of cell pellet (wet weight) were resuspended in 327 ml of buffer A (20 mM KPO4 (pH 6.9), 0.1 mM EDTA, 7 mM β-ME, 5% Glycerol) supplemented to 50 mM NaCl, and broken with a Manton-Gaulin homogenizer. 25 ml of Sigma Protease Inhibitor solution were added after the first pass. The extract was centrifuged at 15,000 g for 40 minutes at 4° C.

The following purification steps were all performed using a Pharmacia AKTA FPLC system. The activity assays were carried out on T7 DNA in order to detect a specific nicking activity at MlyI sites, are sufficiently closely spaced in this; these sites substrate that nicked DNA is fragmented.

The 395 ml of the centrifuged crude cell extract was loaded on a 395 ml Heparin HyperD AP5, which had been equilibrated with buffer A1 (buffer A supplemented with 50 mM NaCl). The column was then washed with 800 ml of buffer A1. The enzyme was eluted with a 3.5 L gradient from 0.05M to 0.7 M NaCl in buffer A (flow rate: 30 ml/min). 15 ml-fractions were collected and assayed for nicking activity. Fractions 96–124 (average salt concentration 330 mM) had the most activity and were pooled and dialyzed against 2l of buffer B (20 mM Tris-HCl (pH 8.0), 0.1 mM EDTA, 7 mM β-ME, 5% Glycerol). A volume of buffer B supplemented with 100 mM NaCl was added to the sample in order to bring the salt concentration to 50 mM.

The sample (850 ml) was then loaded onto an 80 ml (3.5 cm×8.3 cm) Source-15Q Fineline 35 which had been equilibrated with buffer B1 (buffer B supplemented with 50 mM NaCl). The column was then washed with 160 ml of buffer B1. The enzyme was eluted with a 1.5 L gradient from 0.05M to 1M NaCl in buffer B (flow rate: 20 ml/min). 15 ml-fractions were collected and assayed for nicking activity. Fractions 14–19 (average salt concentration 140 mM) had the most activity and were pooled and diluted to 50 mM NaCl with buffer B.

The third column was a 6 ml (1.6 cm×3.0 cm) Source 15S column. It was equilibrated with buffer A1 and the 320 ml sample was loaded to this column. The column was washed with 15 ml of buffer A1 and the enzyme was eluted with a 120 ml gradient from 0.05 mM to 1 M NaCl in buffer A (flow rate: 6 m/min). Three-ml fractions were collected and assayed for nicking activity. However it turned out that the mutant protein did not attached to the resin, so that the active proteins were found in the flow-through and in the wash.

The flow-through and the wash (400 ml) of the Source 15S column were loaded on a 8 ml (1 cm×11.3 cm) Heparin TSK5pw that had been equilibrated with buffer A1. The column was washed with 16 ml of buffer A1 and the enzyme was eluted with a 240 ml gradient from 0.05 mM to 1 M NaCl in buffer A (flow rate: 4 ml/min). Four-ml fractions were collected and assayed for nicking activity. A nicking activity was found in fractions 18–24 (average salt concentration 270 mM). Reducing SDS loading buffer supplemented with 40 mM of DTT (NEB) was added to 20 Al of the peak fractions (18–24) and those samples were denatured at 95° C. for 4 min and loaded on a 10–20% Pre-Cast 10×10 cm SDS-polyacrylamide gel (Owl Separation Systems). The gel was stained using Gel Code Blue Stain (Pierce) and destained with distilled water. The purest fractions (B20–24) were pooled together and dialyzed against storage buffer (50 mM KCl, 10 mM Tris-HCl (pH 7.4), 0.1 mM EDTA, 1 mM dithiothreitol and 50% glycerol)

EXAMPLE 2

Converting the Type IIs Restriction Endonuclease into Nicking Endonuclease by Domain Swapping This novel approach took advantage of the non-functional dimerization domain of a naturally occurring nicking enzyme, N.BstNBI. The dimerization domain of AlwI was replaced by the corresponding domain in N.BstNBI (FIG. 3). The resulting recombinant endonuclease shows specific nicking activity towards double-stranded DNA. The domain swapping strategy utilizes the following steps:
1. Amplification of the 5' end of AlwI by PCR.

Specific primers were designed based on the wild-type AlwI sequence. The forward primer (SEQ ID NO:9) contained an AgeI restriction site to facilitate cloning. The reverse primer (SEQ ID NO: 10) has 21 nucleotides (1 to 21) complementary to the nucleotide sequence of N.BstNBI from 1387 to 1407.

5'-TTACCGGTAAGGAGGTGATCTAATGAGCACGTGGCTTCTTGGAA (SEQ ID NO:9)

5'-TTCACCAAGAACAATAAAGTCTTCATACTCAAAGATCACATCAG (SEQ ID NO:10)

These two primers were used to amplify the 5' region of AlwI from pLT7K-AlwIR (K. Lunnen and G. Wilson, New England Biolabs) by combining:

10 µl 10x PCR buffer (Perkin Elmer)
5 µl 2 mM dNTPs
2 µl (100 ng) pLT7K-AlwIR
0.2 µl (1 unit) Taq Polymerase (Perkin Elmer)
0.2 µl (0.1 unit) Deep Vent® polymerase (New England Biolabs)
5 µl (20 µM) forward primer (SEQ ID NO:9)
5 µl (20 µM) reverse primer (SEQ ID NO:10)
73 µl ddH$_2$O The amplification was carried out 15 cycles at 95° C. for 30 seconds, 50° C. for 30 seconds, and 72° C. for 1 minute. The amplification product was purified and eluted into 30 µl ddH$_2$O using the Qiagen PCR Purification Kit.
2 Amplification of the 3' end of N.BstNBI by PCR.

Specific primers were designed based on the wild-type N.BstNBI sequence. The forward primer (SEQ ID NO: 11) is complementary to SEQ ID NO: 10. The reverse primer (SEQ ID NO: 12) contained a XhoI restriction site to facilitate cloning.

5'- GACTTTATTGTTCTTGGTGAA (SEQ ID NO: 11)
5'- TTCTCGAGTTAAAACCTTACCTCCTTGTCAACAA (SEQ ID NO: 12)

These two primers were used to amplify the 3' region of the N.BstNBI gene from plasmid pHKT7-n.bstNBI (U.S. Pat. No. 6,191,267) by combining:

10 µl 10x PCR buffer (Perkin Elmer)
5 µl 2 mM dNTPs
5 µl (200 ng) pHKT7-n.bstNBI
0.2 µl (1 unit) Taq Polymerase (Perkin Elmer)
0.2 µl (0.1 unit) Deep Vent® polymerase (New England Biolabs)
5 µl (20 µM) forward primer (SEQ ID NO: 11)
5 µl (20 µM) reverse primer (SEQ ID NO: 12)
70 µl ddH$_2$O The amplification was carried out 15 cycles at 95° C. for 30 seconds, 50° C. for 30 seconds, and 72° C. for 1 minute. The amplification product was purified and eluted into 30 µl ddH$_2$O using the Qiagen PCR Purification Kit.
Assembly of Recombinant N.AlwI Endonuclease Gene and Subsequent Cloning into a Plasmid.

Using PCR products amplified during step 1 and step 2, a 1707 bp-long N.AlwI PCR product (FIG. 2) was generated by the following PCR procedure:

10 µl 10x PCR buffer (Perkin Elmer)

5 μl 2 mM dNTPs

10 μl PCR product from step 1

10 μl PCR product from step 2

0.2 μl (1 unit) Taq Polymerase (Perkin Elmer)

0.2 μl (0.1 unit) Deep Vent® polymerase (New England Biolabs)

5 μl (20 μM) forward primer (SEQ ID NO:9)

5 μl (20 μM) reverse primer (SEQ ID NO:12)

55 μl ddH₂O

The amplification was carried out 15 cycles at 95° C. for 30 seconds, 50° C. for 30 seconds, and 72° C. for 1 minute. The amplification product was purified using the Qiagen PCR Purification Kit. One hundred ng of pLT7K vector (Kong, H. et al., *Nuc. Acids Res.* 28:3216–3223 (2000)) and the N.AlwI PCR product (~100 ng) were both digested with 10 units of AgeI and 10 units of XhoI, supplemented with 0.1 mg/ml BSA in 1X NEB buffer 2 in a 10 μl reaction that was incubated at 37° C. for one hour. The digests were run on a 1% low melting temperature agarose gel (FMC BioProducts) in TAE buffer. The gel slices containing PCR and vector DNA bands were both excised out, diluted in equal volume of TE buffer (10 mM Tris pH 8.0, 1mM EDTA), and incubated at 65° C. for 50 minutes. The in-gel ligation was performed by combining the following:

2 μl prepared pHKUV5 (100 ng)

6 μl PCR product (200 ng)

2 μl 10X T4 DNA Ligase Buffer

1 μl T4 DNA Ligase (400 units)

0.5 μl β-Agarase (0.5 unit)

8.5 μl ddH2O

The reaction was incubated at 37° C. for one hour, and three μl of the ligation reaction was transformed into *E. coli* strain ER2566. Individual colonies were analyzed for the presence of N.AlwI and subsequently sequenced. The plasmid containing the correct N.AlwI sequence was named pAB2.

4. Determination of the Sequence-specific Nicking Activity of N.AlwI.

The expression of N.AlwI protein was induced with 0.3 mM IPTG at 30° C. for 4 hrs. Forty grams *E. coli* strain ER2566 cells, which contain pAB2, were resuspended in 100 ml buffer A(20 mM Tris-HCl pH 7.4, 0.1 mM EDTA, 1 mM dithiothreitol, and 50 mM NaCl), sonicated, and centrifuged at 30,000 g for 30 min at 4° C. The supernatant was loaded on a 30 ml Heparin Hyper D column, which had been equilibrated with buffer A. The column was then washed with 150 ml of buffer A. The enzyme was eluted with a linear gradient of 0.05 M to 1 M NaCl in buffer A. Fractions of 5 ml were collected and assayed for DNA nicking activity. Active fractions were pooled and loaded on a 20 ml Mono-Q column equilibrated with buffer A. After washing with 200 ml buffer A, the enzyme was eluted with a linear gradient of 0.05 M to 0.7 M NaCl in buffer A. Fractions of 3 ml were collected and assayed for nicking activity. Active fractions were pooled and loaded on a 1 ml HPLK column equilibrated with buffer A. The column was washed with 30 ml of buffer A and the enzyme was eluted with a 30 ml gradient from 0.05 mM to 1 M NaCl in buffer A. Fractions of 1 ml were collected and assayed for activity. Active fractions were pooled and dialyzed against storage buffer (50 mM Tris-HCl pH 7.4, 0.1 mM EDTA, 1 mM dithiothreitol, 50 mM NaCl, and 50% glycerol).

After dialysis, the N.AlwI protein reached about 80% purity and was used for the following assays.

To construct a plasmid containing a single AlwI site (5'-GGATC-3'), plasmid pACYC184 (NEB) was digested with SfcI and AvaI, filled in using Klenow enzyme, and self-ligated to generate plasmid pAC1. To obtain a plasmid without any AlwI site, plasmid pACYC184 was digested with SfcI and BsaBI, filled in using Klenow enzyme, and self-ligated to generate plasmid pAC0.

Figure 5A:
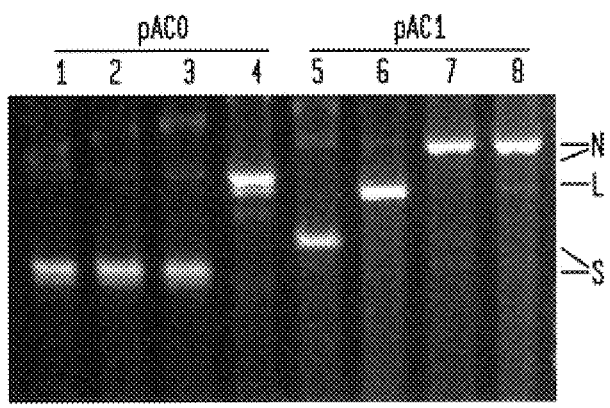
FIG. 5A: N.AlwI cleavage activity on plasmid DNA. Lane 1, supercoiled plasmid pAC0; lane 2, pAC0 digested with AlwI; lane 3, pAC0 digested with N.AlwI; lane 4, pAC0 digested with N.BstNBI; lane 5, supercoiled plasmid pAC1; lane 6, pAC1 digested with AlwI; lane 7, pAC1 digested with N.AlwI; lane 8, pAC1 digested with N.BstNBI. S: supercoiled form of DNA. L: linearized form of DNA. N: nicked form of DNA.
Figure 5B:
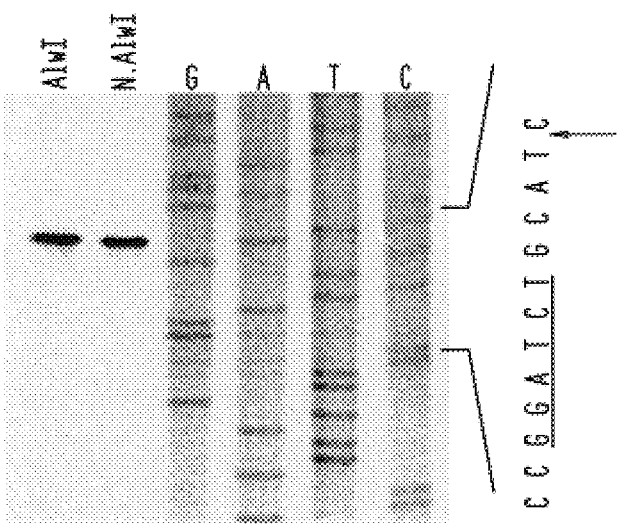
FIG. 5B: Mapping cleavage sites by modified sequencing reactions. Four μg pAC1, containing a single 5'-GGATC-3' sequence, was used in manual sequencing reactions primed by Alw15f. Two additional reactions of the same primer were fully extended without the addition of dideoxynucleotides and then digested with either AlwI or N.AlwI. Reactions were fractionated on an 8% polyacrylamnide gel and detected by autoradiography.
Figure 5C:
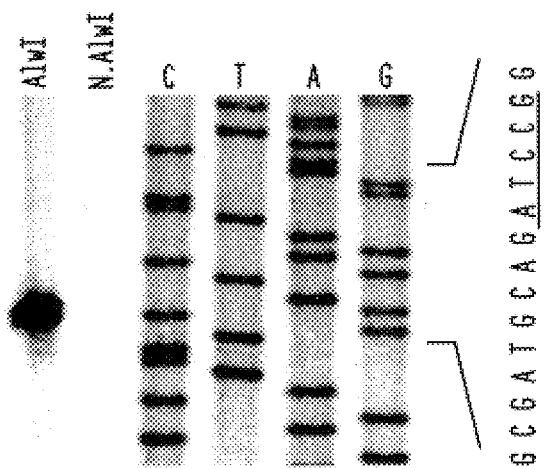
FIG. 5C: Identical to B except that primer Alw16r was used.

As shown in FIG. 5, neither N.AlwI nor AlwI cut plasmid pAC0 due to the absence of recognition sites (FIG. 5A, lane 2 and 3). Therefore, the reaction products migrated similar to the undigested plasmid (FIG. 5A, lane 1). Since there are two N.BstNBI sites on pAC0, N.BstNBI nicked pAC0, relaxing it (FIG. 5A, lane 4). When pAC1 was used as substrate, AlwI cut both strands and linearized it (FIG. 5A, lane 6). In contrast, N.AlwI nicked one strand and generated a relaxed form of pAC1 (FIG. 5A, lane 7), which migrated at the same molecular weight as the relaxed form produced by N.BstNBI (FIG. 5A, lane 8). The result shows that N.AlwI recognizes 5'-GGATC-3' and nicks DNA.

To map the exact nicking site of N.AlwI, the nicking product of N.AlwI-digested pAC1 was fractionated on a polyacrylamide sequencing gel parallel to a sequencing ladder (FIGS. 5B and 5C). Primer Alw15f (SEQ ID NO: 13) was used in the forward reactions (FIG. 5B) and primer Alw16r (SEQ ID NO:14) was used in the reverse reactions (FIG. 5C)

Alw15f 5'-CACGGGGCCTGCCACCATA (SEQ ID NO:13)

Alw16r 5'-AACGGTTAGCGCTTCGTTA (SEQ ID NO: 14)

As illustrated in FIG. 5B, both AlwI and N.AlwI cut the top strand and the cleavage site was located 4 bases away from the recognition site. However, N.AlwI had no cleavage activity towards the bottom strand (FIG. 5C). In contrast, AlwI cut the bottom strand as well. The result suggests the nicking activity of N.AlwI is (5'-GGATCNNN↓ N-3').

A sample of the *E. coli* NEB#1322 which contains plasmid pLT7K-N.AlwI has been deposited under the terms and conditions of the Budapest Treaty with the 10 ° American Type Culture Collection on and received ATCC Accession Number, and a sample of *E. coli* NEB#1367 which contains plasmid pUC 19-MlyIR-Y491 A/K494A has been deposited under the terms and conditions of the Budapest Treaty with the American Type Culture Collection on and received ATCC Accession Number.

What is claimed is:

1. A method for converting a Type IIs restriction endonucleases into a site specific nicking endonucleases, wherein said method comprises disrupting the dimerization function of the Type IIs restriction endonuclease.

2. The method of claim 1, wherein disruption of the Type IIs restriction endonuclease dimerization function comprises substitution of at least one amino acid residue in the dimerization domain of the Type IIs restriction endonuclease.

3. The method of claim 1, wherein disruption of the Type IIs restriction endonuclease dimerization function comprises substituting the Type IIs restriction endonuclease dimerization domain with a second domain corresponding structurally to a dimerization domain, but obtained from a second site-specific endonuclease.

4. The method of claim 3, wherein the second dimerization domain comprises a dimerization domain of a naturally occurring site specific nicking endonuclease.

5. The method of claim 3, wherein the second dimerization domain comprises a genetically modified Type IIs dimerization domain.

6. An AlwI restriction endonuclease which has been converted into a site specific nicking endonuclease.

7. An MlyI restriction endonuclease which has been converted into a site specific nicking endonuclease.

* * * * *

UNITED STATES PATENT AND TRADEMARK OFFICE
CERTIFICATE OF CORRECTION

PATENT NO. : 6,395,523 B1
DATED : May 28, 2002
INVENTOR(S) : Kong et al.

It is certified that error appears in the above-identified patent and that said Letters Patent is hereby corrected as shown below:

Column 1,
Line 50, replace "Komberg" with -- Kornberg --

Column 4,
Line 47, replace "pNB 1" with -- pNB1 --
Line 49, replace "pNBO" with -- pNB0 --

Column 8,
Line 42, replace "α0:5-helix" with -- "α5-helix --

Column 11,
Line 22, replace "ATIT" with -- ATTT --

Column 13,
Line 36, replace "6 m/min" with -- 6 ml/min --
Line 49, replace "20 A1" with -- 20 µl --

Column 14,
Line 62, replace "Assembly" with -- 3. Assembly --

Column 15,
Line 23, replace "ImM" with -- 1mM --

Column 16,
Line 50, delete "10 º"

Signed and Sealed this

Twentieth Day of May, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,395,523 B1 Page 1 of 1
DATED : May 28, 2002
INVENTOR(S) : Huimin Kong et al.

It is certified that error appears in the above-identified patent and that said Letters Patent is hereby corrected as shown below:

Column 1,
Line 5, please insert the following:

-- Government Support

Work described herein was supported by the National Institute of General Medical Sciences of the National Institutes of Health under Grant No. 5 R44 GM60057-03. The United States Government may have certain rights in the invention. --

Signed and Sealed this

Twenty-third Day of December, 2003

JAMES E. ROGAN
*Director of the United States Patent and Trademark Office*

SEQUENCE LISTING

<160> NUMBER OF SEQ ID NOS: 14

<210> SEQ ID NO 1
<211> LENGTH: 19
<212> TYPE: DNA

-continued

```
<213> ORGANISM: Micrococcus lylae
<220> FEATURE:
<223> OTHER INFORMATION: N = any nucleotide

<400> SEQUENCE: 1
nnnnnngagt cnnnnnnnn                                                    19

<210> SEQ ID NO 2
<211> LENGTH: 19
<212> TYPE: DNA
<213> ORGANISM: Acinetobacter lwoffii
<220> FEATURE:
<223> OTHER INFORMATION: N = any nucleotide

<400> SEQUENCE: 2
nnnnnnggat cnnnnnnnn                                                    19

<210> SEQ ID NO 3
<211> LENGTH: 556
<212> TYPE: PRT
<213> ORGANISM: Micrococcus lylae
<220> FEATURE:
<223> OTHER INFORMATION: X at position 295 a nd 302 = any amino acid

<400> SEQUENCE: 3
```

Met Ala Ser Leu Ser Lys Thr Lys His Leu P he Gly Phe Thr Ser Pro
 1               5                  10                  15

Arg Thr Ile Glu Lys Ile Ile Pro Glu Leu A sp Ile Leu Ser Gln Gln
            20                  25                  30

Phe Ser Gly Lys Val Trp Gly Glu Asn Gln I le Asn Phe Phe Asp Ala
        35                  40                  45

Ile Phe Asn Ser Asp Phe Tyr Glu Gly Thr T hr Tyr Pro Gln Asp Pro
    50                  55                  60

Ala Leu Ala Ala Arg Asp Arg Ile Thr Arg A la Pro Lys Ala Leu Gly
65                  70                  75                  80

Phe Ile Gln Leu Lys Pro Val Ile Gln Leu T hr Lys Ala Gly Asn Gln
                85                  90                  95

Leu Val Asn Gln Lys Arg Leu Pro Glu Leu P he Thr Lys Gln Leu Leu
            100                 105                 110

Lys Phe Gln Leu Pro Ser Pro Tyr His Thr G ln Ser Pro Thr Val Asn
        115                 120                 125

Phe Asn Val Arg Pro Tyr Leu Glu Leu Leu A rg Leu Ile Asn Glu Leu
    130                 135                 140

Gly Ser Ile Ser Lys Thr Glu Ile Ala Leu P he Phe Leu Gln Leu Val
145                 150                 155                 160

Asn Tyr Asn Lys Phe Asp Glu Ile Lys Asn L ys Ile Leu Lys Phe Arg
                165                 170                 175

Glu Thr Arg Lys Asn Asn Arg Ser Val Ser T rp Lys Thr Tyr Val Ser
            180                 185                 190

Gln Glu Phe Glu Lys Gln Ile Ser Ile Pro A la Asp Glu Val Thr
        195                 200                 205

Ala Lys Asn Phe Arg Thr Arg Glu Ser Ser A sp Glu Ser Phe Lys Lys
    210                 215                 220

Phe Val Lys Thr Lys Glu Gly Asn Met Lys A sp Tyr Ala Asp Ala Phe
225                 230                 235                 240

Phe Arg Tyr Ile Arg Gly Thr Gln Leu Val T hr Ile Asp Lys Asn Leu
                245                 250                 255

His Leu Lys Ile Ser Ser Leu Lys Gln Asp S er Val Asp Phe Leu Leu

```
                    260                 265                 270
Lys Asn Thr Asp Arg Asn Ala Leu Asn Leu S er Leu Met Glu Tyr Glu
            275                 280                 285

Asn Tyr Leu Phe Asp Pro Xaa Gln Leu Ile V al Leu Glu Xaa Asn Ser
        290                 295                 300

Gly Leu Ile Asn Ser Lys Ile Lys Gln Leu A sp Asp Ser Ile Asn Val
305                 310                 315                 320

Glu Ser Leu Lys Ile Asp Asp Ala Lys Asp L eu Leu Asn Asp Leu Glu
                325                 330                 335

Ile Gln Arg Lys Ala Lys Thr Ile Glu Asp T hr Val Asn His Leu Lys
            340                 345                 350

Leu Arg Ser Asp Ile Glu Asp Ile Leu Asp V al Phe Ala Lys Ile Lys
        355                 360                 365

Lys Arg Asp Val Pro Asp Val Pro Leu Phe L eu Glu Trp Asn Ile Trp
    370                 375                 380

Arg Ala Phe Ala Ala Leu Asn His Thr Gln A la Ile Glu Gly Asn Phe
385                 390                 395                 400

Ile Val Asp Leu Asp Gly Met Pro Leu Asn T hr Ala Pro Gly Lys Lys
                405                 410                 415

Pro Asp Ile Glu Ile Asn Tyr Gly Ser Phe S er Cys Ile Val Glu Val
            420                 425                 430

Thr Met Ser Ser Gly Glu Thr Gln Phe Asn M et Glu Gly Ser Ser Val
        435                 440                 445

Pro Arg His Tyr Gly Asp Leu Val Arg Lys V al Asp His Asp Ala Tyr
    450                 455                 460

Cys Ile Phe Ile Ala Pro Lys Val Ala Pro G ly Thr Lys Ala His Phe
465                 470                 475                 480

Phe Asn Leu Asn Arg Leu Ser Thr Lys His T yr Gly Gly Lys Thr Lys
                485                 490                 495

Ile Ile Pro Met Ser Leu Asp Asp Phe Ile C ys Phe Leu Gln Val Gly
            500                 505                 510

Ile Thr His Asn Phe Gln Asp Ile Asn Lys L eu Lys Asn Trp Leu Asp
        515                 520                 525

Asn Leu Ile Asn Phe Asn Leu Glu Ser Glu A sp Glu Glu Ile Trp Phe
    530                 535                 540

Glu Glu Ile Ile Ser Lys Ile Ser Thr Trp A la Ile
545                 550                 555

<210> SEQ ID NO 4
<211> LENGTH: 604
<212> TYPE: PRT
<213> ORGANISM: Bacillus stearothermophilus

<400> SEQUENCE: 4

Met Ala Lys Lys Val Asn Trp Tyr Val Ser C ys Ser Pro Arg Ser Pro
1               5                   10                  15

Glu Lys Ile Gln Pro Glu Leu Lys Val Leu A la Asn Phe Glu Gly Ser
            20                  25                  30

Tyr Trp Lys Gly Val Lys Gly Tyr Lys Ala G ln Glu Ala Phe Ala Lys
        35                  40                  45

Glu Leu Ala Ala Leu Pro Gln Phe Leu Gly T hr Thr Tyr Lys Lys Glu
    50                  55                  60

Ala Ala Phe Ser Thr Arg Asp Arg Val Ala P ro Met Lys Thr Tyr Gly
65                  70                  75                  80
```

```
Phe Val Phe Val Asp Glu Glu Gly Tyr Leu Arg Ile Thr Glu Ala Gly
                85                  90                  95

Lys Met Leu Ala Asn Asn Arg Arg Pro Lys Asp Val Phe Leu Lys Gln
            100                 105                 110

Leu Val Lys Trp Gln Tyr Pro Ser Phe Gln His Lys Gly Lys Glu Tyr
        115                 120                 125

Pro Glu Glu Glu Trp Ser Ile Asn Pro Leu Val Phe Val Leu Ser Leu
    130                 135                 140

Leu Lys Lys Val Gly Gly Leu Ser Lys Leu Asp Ile Ala Met Phe Cys
145                 150                 155                 160

Leu Thr Ala Thr Asn Asn Asn Gln Val Asp Glu Ile Ala Glu Glu Ile
                165                 170                 175

Met Gln Phe Arg Asn Glu Arg Glu Lys Ile Lys Gly Gln Asn Lys Lys
            180                 185                 190

Leu Glu Phe Thr Glu Asn Tyr Phe Phe Lys Arg Phe Glu Lys Ile Tyr
        195                 200                 205

Gly Asn Val Gly Lys Ile Arg Glu Gly Lys Ser Asp Ser Ser His Lys
    210                 215                 220

Ser Lys Ile Glu Thr Lys Met Arg Asn Ala Arg Asp Val Ala Asp Ala
225                 230                 235                 240

Thr Thr Arg Tyr Phe Arg Tyr Thr Gly Leu Phe Val Ala Arg Gly Asn
                245                 250                 255

Gln Leu Val Leu Asn Pro Glu Lys Ser Asp Leu Ile Asp Glu Ile Ile
            260                 265                 270

Ser Ser Ser Lys Val Val Lys Asn Tyr Thr Arg Val Glu Glu Phe His
        275                 280                 285

Glu Tyr Tyr Gly Asn Pro Ser Leu Pro Gln Phe Ser Phe Glu Thr Lys
    290                 295                 300

Glu Gln Leu Leu Asp Leu Ala His Arg Ile Arg Asp Glu Asn Thr Arg
305                 310                 315                 320

Leu Ala Glu Gln Leu Val Glu His Phe Pro Asn Val Lys Val Glu Ile
                325                 330                 335

Gln Val Leu Glu Asp Ile Tyr Asn Ser Leu Asn Lys Lys Val Asp Val
            340                 345                 350

Glu Thr Leu Lys Asp Val Ile Tyr His Ala Lys Glu Leu Gln Leu Glu
        355                 360                 365

Leu Lys Lys Lys Lys Leu Gln Ala Asp Phe Asn Asp Pro Arg Gln Leu
    370                 375                 380

Glu Glu Val Ile Asp Leu Leu Glu Val Tyr His Glu Lys Lys Asn Val
385                 390                 395                 400

Ile Glu Glu Lys Ile Lys Ala Arg Phe Ile Ala Asn Lys Asn Thr Val
                405                 410                 415

Phe Glu Trp Leu Thr Trp Asn Gly Phe Ile Ile Leu Gly Asn Ala Leu
            420                 425                 430

Glu Tyr Lys Asn Asn Phe Val Ile Asp Glu Glu Leu Gln Pro Val Thr
        435                 440                 445

His Ala Ala Gly Asn Gln Pro Asp Met Glu Ile Ile Tyr Glu Asp Phe
    450                 455                 460

Ile Val Leu Gly Glu Val Thr Thr Ser Lys Gly Ala Thr Gln Phe Lys
465                 470                 475                 480

Met Glu Ser Glu Pro Val Thr Arg His Tyr Leu Asn Lys Lys Lys Glu
                485                 490                 495

Leu Glu Lys Gln Gly Val Glu Lys Glu Leu Tyr Cys Leu Phe Ile Ala
```

```
              500             505             510
Pro Glu Ile Asn Lys Asn Thr Phe Glu Glu Phe Met Lys Tyr Asn Ile
        515                 520             525

Val Gln Asn Thr Arg Ile Ile Pro Leu Ser Leu Lys Gln Phe Asn Met
    530                 535             540

Leu Leu Met Val Gln Lys Lys Leu Ile Glu Lys Gly Arg Arg Leu Ser
545             550                 555                 560

Ser Tyr Asp Ile Lys Asn Leu Met Val Ser Leu Tyr Arg Thr Thr Ile
            565                 570                 575

Glu Cys Glu Arg Lys Tyr Thr Gln Ile Lys Ala Gly Leu Glu Glu Thr
        580                 585             590

Leu Asn Asn Trp Val Val Asp Lys Glu Val Arg Phe
        595                 600

<210> SEQ ID NO 5
<211> LENGTH: 43
<212> TYPE: DNA
<213> ORGANISM: Micrococcus lylae

<400> SEQUENCE: 5
ttaagcttaa ggaggtgatc taatggcatc gttatcaaag act                    43

<210> SEQ ID NO 6
<211> LENGTH: 30
<212> TYPE: DNA
<213> ORGANISM: Micrococcus lylae

<400> SEQUENCE: 6
ggaataatct tgttgctcc accagcatgt                                    30

<210> SEQ ID NO 7
<211> LENGTH: 32
<212> TYPE: DNA
<213> ORGANISM: Micrococcus lylae

<400> SEQUENCE: 7
atttctagac tatatagccc atgtagaaat tt                                32

<210> SEQ ID NO 8
<211> LENGTH: 30
<212> TYPE: DNA
<213> ORGANISM: Micrococcus lylae

<400> SEQUENCE: 8
acatgctggt ggagcaacaa agattattcc                                   30

<210> SEQ ID NO 9
<211> LENGTH: 44
<212> TYPE: DNA
<213> ORGANISM: Acinetobacter lwoffii

<400> SEQUENCE: 9
ttaccggtaa ggaggtgatc taatgagcac gtggcttctt ggaa                   44

<210> SEQ ID NO 10
<211> LENGTH: 44
<212> TYPE: DNA
<213> ORGANISM: Unknown
<220> FEATURE:
<223> OTHER INFORMATION: Description of Unknown Organism: Position
      1-16 are from Bacillus stearothermo philus and position 17-44 are
      from Acinetobacter lwoffii. These are fused together.
```

```
<400> SEQUENCE: 10
ttcaccaaga acaataaagt cttcatactc aaagatcaca tcag                    44

<210> SEQ ID NO 11
<211> LENGTH: 21
<212> TYPE: DNA
<213> ORGANISM: Bacillus stearothermophilus

<400> SEQUENCE: 11
gactttattg ttcttggtga a                                             21

<210> SEQ ID NO 12
<211> LENGTH: 34
<212> TYPE: DNA
<213> ORGANISM: Bacillus stearothermophilus

<400> SEQUENCE: 12
ttctcgagtt aaaaccttac ctccttgtca acaa                               34

<210> SEQ ID NO 13
<211> LENGTH: 19
<212> TYPE: DNA
<213> ORGANISM: Escherichia coli

<400> SEQUENCE: 13
cacggggcct gccaccata                                                19

<210> SEQ ID NO 14
<211> LENGTH: 19
<212> TYPE: DNA
<213> ORGANISM: Escherichia coli

<400> SEQUENCE: 14
aacggttagc gcttcgtta                                                19
```